United States Patent
Zhu et al.

(10) Patent No.: US 8,859,527 B2
(45) Date of Patent: Oct. 14, 2014

(54) INCLUSION COMPLEX OF DEOXYPODOPHYLLOTOXIN OF CYCLODEXTRIN, PREPARATION METHOD, USE FOR TREATMENT OF CANCER THEREOF

(75) Inventors: Xiong Zhu, Jiangsu (CN); Jinlong Huang, Zhejiang (CN); Baojin Wu, Jiangsu (CN); Houwei Luo, Jiangsu (CN); Zhiwu Yin, Zhejiang (CN); Changxuan Wu, Jiangsu (CN)

(73) Assignees: Zhejiang Jianfeng Pharmaceutical Holdings (CN); China Pharmaceutical University (CN)

( * ) Notice: Subject to any disclaimer, the term of this patent is extended or adjusted under 35 U.S.C. 154(b) by 0 days.

(21) Appl. No.: 13/502,092

(22) PCT Filed: Oct. 1, 2010

(86) PCT No.: PCT/CN2010/077554
§ 371 (c)(1),
(2), (4) Date: May 24, 2012

(87) PCT Pub. No.: WO2011/044824
PCT Pub. Date: Apr. 21, 2011

(65) Prior Publication Data
US 2012/0225934 A1    Sep. 6, 2012

(30) Foreign Application Priority Data

Oct. 15, 2009   (CN) .......................... 2009 1 0035978

(51) Int. Cl.
| | |
|---|---|
| *A61K 47/48* | (2006.01) |
| *A61K 31/365* | (2006.01) |
| *B82Y 5/00* | (2011.01) |
| *C08B 37/16* | (2006.01) |
| *C08L 5/16* | (2006.01) |
| *A61K 31/724* | (2006.01) |

(52) U.S. Cl.
CPC ......... *A61K 47/48969* (2013.01); *A61K 31/724* (2013.01); *A61K 31/365* (2013.01); *B82Y 5/00* (2013.01); *C08B 37/0015* (2013.01); *C08L 5/16* (2013.01)
USPC ........................................... 514/58; 514/463

(58) Field of Classification Search
CPC ................................................ A61K 31/724
USPC .................................................. 514/58, 463
See application file for complete search history.

(56) References Cited

FOREIGN PATENT DOCUMENTS

| | | | |
|---|---|---|---|
| CN | 1879887 | 6/2003 | ............. A61K 47/40 |
| CN | 1424112 | 12/2006 | ............. A61K 47/40 |

OTHER PUBLICATIONS

Van Uden et al., "The production of podophyllotoxin and its 5-methoxy derivative through bioconversion of cyclodextrin-complexed desoxypodophyllotoxin by plant cell cultures", Plant Cell, Tissue and Organ Culture, vol. 42, No. 1, pp. 73-79 (1995).*
Cserháti et al., "Interaction of taxol and other anticancer drugs with hydroxypropyl-β-cyclodextrin", International Journal of Pharmaceutics, vol. 108, No. 1, pp. 69-75 (1994).(see enclosed abstract).*
International Search Report issued in corresponding Chinese patent application No. PCT/CN2010/077554 dated Jan. 6, 2011 (with translation) (6 pgs).

* cited by examiner

*Primary Examiner* — Kevin E Weddington
(74) *Attorney, Agent, or Firm* — Hayes Soloway P.C.

(57) ABSTRACT

Inclusion complex of deoxypodophyllotoxin of cyclodextrin, the preparation method and the use for the treatment of cancer thereof are disclosed. The inclusion complex consists of deoxypodophyllotoxin and beta-cyclodextrin derivative, wherein the molar ration of deoxypodophyllotoxin to beta-cyclodextrin derivative is 1:1-1:10. The beta-cyclodextrin derivative is sulfobutyl ether-beta-cyclodextrin or hydroxypropyl-beta-cyclodextrin.

6 Claims, 2 Drawing Sheets

INCLUSION COMPLEX OF DEOXYPODOPHYLLOTOXIN OF CYCLODEXTRIN, PREPARATION METHOD, USE FOR TREATMENT OF CANCER THEREOF

FIELD OF THE INVENTION

This invention relates to the pharmaceutical field, in particular relates to inclusion complex of deoxypodophyllotoxin of cyclodextrin, preparation method, the use for treatment of cancer thereof.

BACKGROUND OF THE INVENTION

Deoxypodophyllotoxin (DPT) is a compound extracted and purified from the traditional Chinese medicine Sinopodophyllum emodi (Wall.). It has been reported as early as 1990's that DPT has an in vitro inhibition effects on the cell lines of P-388 leukemia, human lung cancer A-549 and colon cancer HT-29 (Arch Pharm (Weinheim). 1994 March; 327 (3): 157~9. Planta Med. 1993 June; 59 (3): 246~9), but the studies only focus on the experiments on its in vitro activities. Experiments on in vivo activities have not been reported for more than ten years, which can be mainly attributed to that this compound is insoluble in water and can not be used to produce the preparations for intravenous injection. A series of glycoside derivatives were synthesized by using the hydroxyl group of position 4 in Podophyllotoxin in the 1970's, wherein the well known Etopside and Teniposide have been successfully applied to clinical practices. However, hydroxyl group is absent at the position 4 in DPT. Thus DPT can not be used to prepare glycoside derivative. It has become a key project for scientists that how to use DPT prepare injections thereof to validate its in vivo anti-cancer activities in animals and further apply it into clinical practices.

SUMMARY OF THE INVENTION

The object of this invention is to provide a water-soluble deoxypodophyllotoxin preparation (it is abbreviated as DPI hereafter) in order to carry out in vivo and in vitro experiments in animals using the same, and further develop drugs for treating different kinds of cancers.

The solubility of DPT in water is about 0.5 mg/L and it is almost insoluble. The present invention prepares the DPT inclusion complex with relatively good water solubility by including DPT with β-cyclodextrin (β-CD) derivative. The experiments show that during the preparation of DPT inclusion complex, the efficacy for the inclusion complex prepared by using the hydrophilic derivative of β-CD hydroxypropyl-β-cyclodextrin (HP-β-CD) and its ionic derivative sulfobutyl ether-β-cyclodextrin (SBE-β-CD) was significantly better than that of other β-CD derivatives, and the resultant inclusion complex have extremely high water-solubility, which can meet the requirements for in vivo anti-cancer activity tests in animals. On the basis of this, preferably the molar ratio of deoxypodophyllotoxin to β-cyclodextrin derivative is from 1:1 to 1:10, and the β-cyclodextrin derivative described below in the present invention is sulfobutyl ether-β-cyclodextrin or hydroxypropyl β-cyclodextrin.

The experiments show that different molar ratios of β-cyclodextrin to DPT in the inclusion complexes may lead to different solubility of DPT. HP-β-CD and DPT are prepared into inclusion complexes under different conditions, and the DPT concentration in the inclusion complex is determined by ultraviolet spectrophotometry, and the composition molar ratio of DPT to HP-β-CD in the inclusion complex is further calculated; the water-solubility of the inclusion complex is determined according to the method specified in the examples of Chinese Pharmacopoeia 2005, so that solubility of DPT in this inclusion complex is further calculated. The results are shown in Table 1.

TABLE 1

Composition and solubility of the inclusion complex of DPT and HP-β-CD

| Sample Nmber | DPT:HP-β-CD (molar ratio) | DPT solubility (mg/L) |
|---|---|---|
| 1 | 1:0.54 | 45.8 |
| 2 | 1:0.82 | 62.5 |
| 3 | 1:1.08 | 145 |
| 4 | 1:1.65 | 263 |
| 5 | 1:2.24 | 597 |
| 6 | 1:4.06 | 882 |
| 7 | 1:6.35 | 1018 |
| 8 | 1:10.1 | 1142 |
| 9 | 1:13.6 | 1208 |
| 10 | 1:15.3 | 1247 |

It can be seen from Table 1 that the solubility of DPI gradually increases as the proportion of HP-β-CD in the inclusion complex gradually increases When the molar ratio of HP-β-CD to DPT is 2.24:1 in the inclusion complex, the solubility of DPT increases to 597 mg/L, which can meet the requirement for in vivo pharmacodynamic test. When the molar ratio of HP-β-CD to DPT is higher than 6.35:1 in the inclusion complex, the relative degree of increase is very small though the solubility of DPT slightly increases; more importantly, the extremely high concentration of HP-β-CD in the reaction solution leads to extremely high viscosity in the reaction system, filtration, concentration and drying process are difficult and the operability is poor. Therefore, the molar ratio of DPT to HP-β-CD is preferably from 1:2.24 to 1:6.35 when using DPT and HP-β-CD to prepare the inclusion complex.

When SBE-β-CD is selected for the inclusion of DPT, likewise, different molar ratio of SBE-β-CD to DPT in the inclusion complex may lead to different solubility of DPT, as shown in Table 2.

TABLE 2

Composition and solubility of the inclusion complex of DPT with SBE-β-CD

| Sample Number | DPT:SBE-β-CD (molar ratio) | DPT solubility (mg/L) |
|---|---|---|
| 1 | 1:0.48 | 108 |
| 2 | 1:0.72 | 182 |
| 3 | 1:1.00 | 615 |
| 4 | 1:2.33 | 1238 |
| 5 | 1:3.27 | 2351 |
| 6 | 1:6.42 | 5938 |
| 7 | 1:8.06 | 8154 |
| 8 | 1:11.9 | 9806 |
| 9 | 1:13.4 | 10620 |
| 10 | 1:15.6 | 11385 |

It can be seen from Table 2 that the solubility of DPT gradually increases as the proportion of SBE-β-CD in the inclusion gradually increases. When the molar ratio of SBE-β-CD to DPT in the inclusion complex is 1.00:1, the solubility of DPT increases to 615 mg/L, which can meet the requirements for in vivo pharmacodynamic test. When the molar ratio of SBE-β-CD to DPT in the inclusion complex is higher than 8.06, the relatively degree of increase is very small though the solubility of DPT still slightly increases; more importantly, the viscosity of the reaction solution is very high, filtration, concentration and drying process are very difficult and the operability is poor. Therefore, the molar ratio of DPI to SBE-β-CD is preferably from 1:1.00 to 1:8.06 when using DPT and HP-β-CD to prepare the inclusion complex.

Comparing Table 1 with Table 2, the solubilization of SBE-β-CD for DPT is higher than that of HP-β-CD. Therefore, the inclusion complex of SBE-β-CD and DPT is selected for the in vivo and in vitro anticancer activity tests.

The preparation method for the inclusion complex in the present invention comprises: preparing aqueous solution of β-CD derivative, then agitating or grinding and keeping warm, preparing ethanol, acetone or methanol solutions of DPT, dropping the obtained DPT into the aqueous solution of β-cyclodextrin derivative, afterwards continue agitating or grinding and keeping warm, drying to obtain the inclusion complex.

Wherein, the concentration of the aqueous solution prepared with β-CD derivative is preferably 30%~40% which is a weight volume percentage.

Wherein, the temperature for inclusion is preferably 40~70° C. More preferably, the temperature is 50~55° C.

Wherein, the organic solvent is preferably ethanol.

Wherein, the time for continuous agitation or grinding after the DPT solution is dropped into is preferably 0.5~3 hours, more preferably, the time is 1~2 hours.

The tests show that the results are different as the DPT-β-CD inclusion complex prepared under different conditions.

Preparation of DPT-HP-β-CD inclusion complex:

It is prepared by aqueous solution agitation-decompressed concentration-drying, and the operations are as follows:

100 ml HP-β-CD aqueous solutions at different concentrations are prepared and subjected to heated magnetic agitation in beakers, the DPT in ethanol solution is added (DPT and HP-β-CD are added in a molar ratio of 1:2); then the solutions were continuously incubated and agitated for some time, and the solutions were filtrated with filter membrane of 0.45 μm in hot state, the unincluded DPT is removed, the filtrate was subjected to vacuum to dry by membrane spinning decompressed concentration, and finally the white solid was obtained.

With regard to the three factors, namely the concentration of HP-β-CD solution, the temperature for inclusion and the duration for inclusion, orthogonal experiments are carried out on three levels (the concentrations of the HP-β-CD solutions are 10%, 20% and 30%; the temperatures are 40° C., 50° C. and 60° C.; the duration is 1 hour, 2 hour and 3 hour), content and solubility of DPT in the inclusion complex are used as the evaluation parameters for the efficacy of inclusion, and the results are shown in Table 3. The solubility is determined by the method specified in the examples in Chinese Pharmacopoeia 2005, and the results are shown in Table 4.

It is concluded from the range (R) values for the integrative scores in Table 3, HP-β-CD concentration exerts the most significant influence on the inclusion efficacy among the three factors, wherein, the concentration is preferably 30%; the influence of the temperature for inclusion ranks the second, wherein, the temperature is preferably 50° C.; the influence of the time for inclusion is the third wherein, the duration is preferably 1 hour. Therefore, the optimal conditions for inclusion are as follows: 30% HP-β-CD aqueous solution, the temperature for inclusion is 50° C., and the solution is continuously agitated for 1 hour after the ethanol solution of DPT is dropped.

The molar ratio of DPT to HP-β-CD in the nine samples as mentioned above is from 1:2.07 to 1:2.40 and 1:2.24 in average; the solubility is 352~943 mg/L and 597 mg/L in average.

TABLE 3

Results for the orthogonal test on the DPT-HP-β-CD inclusion

| Factors | | 1<br>HP-β-CD<br>(%, g/ml) | 2<br>Temperature<br>for the<br>inclusion(° C.) | 3<br>Time for<br>the<br>inclusion<br>(h) | Drug<br>content (%,<br>g/g) | Solubility<br>(%, mg/ml) | Integrative<br>score |
|---|---|---|---|---|---|---|---|
| Serial | 1 | 10 | 40 | 1 | 10.90 | 37.4 | 29.45 |
| number | 2 | 10 | 50 | 2 | 11.38 | 40.0 | 31.41 |
| for the | 3 | 10 | 60 | 3 | 11.45 | 35.2 | 28.08 |
| test | 4 | 20 | 40 | 2 | 11.76 | 55.1 | 42.10 |
|  | 5 | 20 | 50 | 3 | 10.86 | 60.2 | 45.40 |
|  | 6 | 20 | 60 | 1 | 11.68 | 52.1 | 39.97 |
|  | 7 | 30 | 40 | 3 | 12.08 | 79.6 | 59.34 |
|  | 8 | 30 | 50 | 1 | 12.38 | 94.3 | 69.72 |
|  | 9 | 30 | 60 | 2 | 11.85 | 83.4 | 61.66 |
| K1 |  | 88.94 | 130.89 | 139.14 |  |  |  |
| K2 |  | 127.47 | 146.53 | 135.17 |  |  |  |
| K3 |  | 190.72 | 129.71 | 132.82 |  |  |  |
| R |  | 101.78 | 16.82 | 6.32 |  |  |  |

Note:
integrative score = solubility × 0.7 + drug content × 0.3.

The purpose of inclusion is to increase its solubility and thus the weight thereof is set as 0.7.

TABLE 4

Results for the solubility test of the DPT-HP-β-CD inclusion

| Sample<br>Number | Sampling<br>amount of the<br>sample (mg) | The content<br>of DPT (mg) | Volume of water<br>for complete<br>dissolution (ml) | Solubility<br>(mg/L) |
|---|---|---|---|---|
| 1 | 99.5 | 10.85 | 29.0 | 374 |
| 2 | 91.3 | 10.39 | 26.0 | 400 |

TABLE 4-continued

Results for the solubility test of the DPT-HP-β-CD inclusion

| Sample Number | Sampling amount of the sample (mg) | The content of DPT (mg) | Volume of water for complete dissolution (ml) | Solubility (mg/L) |
|---|---|---|---|---|
| 3 | 87.6 | 10.03 | 28.5 | 352 |
| 4 | 86.7 | 10.20 | 18.5 | 551 |
| 5 | 105.3 | 11.44 | 19.0 | 602 |
| 6 | 91.5 | 10.69 | 20.5 | 521 |
| 7 | 98.8 | 11.94 | 15.0 | 796 |
| 8 | 110.5 | 13.68 | 14.5 | 943 |
| 9 | 84.5 | 10.01 | 12.0 | 834 |

Preparation of the DPT-SBE-β-CD inclusion complex:

It is prepared by the aqueous solution agitation-lyophilization method and the operations are as follows:

100 ml SBE-β-CD aqueous solutions at different concentrations are prepared and are subjected to heated magnetic agitation in beakers, the DPT in acetone solution is added (DPT and HP-β-CD are added into in a molar ratio of 1:3); then the solutions were continuously incubated and agitated for some time, then the solutions are kept at room temperature for 2 hours, the solutions were filtrated by 0.45 μm of, filter membrane, and the filtrate is pre-frozen for 12 hours in a refrigerator and subjected to a lyophilizer to lyophilization for 48 h, and finally the white solid was obtained.

With regard to the three factors, namely the concentration of SBE-β-CD solution, the temperature for inclusion and the duration for inclusion, orthogonal experiments are carried out on three levels (the concentrations of the SBE-β-CD solutions are 10%, 25% and 40%; the temperatures are 40° C., 55° C. and 70° C.; the duration is 0.5 hour, 1 hour and 2 hours), content and solubility of DPT in the inclusion complex are used as the evaluation parameters for the efficacy of inclusion, and the results are shown in Table 5. The DPT content in the inclusion complex is determined by ultraviolet spectrophotometry. The solubility is determined by using the method specified in the examples in Chinese Pharmacopoeia 2005, and the results are shown in Table 6.

The purpose of inclusion is to increase its solubility and thus the weight thereof is set as 0.7.

TABLE 6

Results for the solubility test of the DPT-SBE-β-CD inclusion

| Sample Number | Sampling amount of the sample (mg) | The content of DPT (mg) | Volume of water for complete dissolution (ml) | Solubility (mg/L) |
|---|---|---|---|---|
| 1 | 188 | 10.90 | 14.8 | 736 |
| 2 | 175 | 11.06 | 13.5 | 819 |
| 3 | 170 | 9.42 | 13.8 | 683 |
| 4 | 192 | 10.33 | 6.50 | 1589 |
| 5 | 185 | 10.95 | 6.25 | 1752 |
| 6 | 198 | 9.59 | 6.35 | 1510 |
| 7 | 210 | 10.21 | 2.30 | 4439 |
| 8 | 205 | 10.70 | 2.10 | 5095 |
| 9 | 195 | 8.85 | 1.95 | 4538 |

It is concluded from the range (R) values for the integrative score in Table 5, SBE-β-CD concentration exertes the most significant influence on the inclusion efficacy among the three factors, wherein, the concentration is preferably 40%; the influence of the temperature for inclusion ranks the second, wherein, the temperature is preferably 55° C.; the influence of the time for inclusion is the third, wherein, the duration is preferably 2 hours, therefore, the optimal conditions for inclusion are as follows: 40% SBE-β-CD aqueous solution, the temperature for inclusion is 55° C., and the solution is continuously agitated for 2 hours after the acetone solution of DPT is dropped.

The molar ratio of DPT to SBE-β-CD in the nine samples as mentioned above is from 1:2.74 to 1:3.89 and 1:3.27 in average; the solubility is from 736 to 5095 mg/L and 2351 mg/L in average.

In the in vitro activity test on one kind of animal tumor cell and six kinds of human tumor cells by using the inclusion-

TABLE 5

Results for the orthogonal test on the DPT-SBE-β-CD inclusion

| Factors | | Column Number | | | Results | | |
|---|---|---|---|---|---|---|---|
| | | 1 SBE-β-CD (%, g/ml) | 2 Temperature for the inclusion (° C.) | 3 Time for the inclusion (h) | Drug content (%, g/g) | Solubility (%, mg/ml) | Integrative score |
| Serial number for the test | 1 | 10 | 40 | 0.5 | 5.80 | 73.6 | 53.26 |
| | 2 | 10 | 55 | 1 | 6.32 | 81.9 | 59.23 |
| | 3 | 10 | 70 | 2 | 5.54 | 68.3 | 49.47 |
| | 4 | 25 | 40 | 2 | 5.38 | 158.9 | 112.8 |
| | 5 | 25 | 55 | 0.5 | 5.92 | 175.2 | 124.4 |
| | 6 | 25 | 70 | 1 | 5.03 | 151.0 | 107.2 |
| | 7 | 40 | 40 | 1 | 4.86 | 443.9 | 312.2 |
| | 8 | 40 | 55 | 2 | 5.22 | 509.5 | 358.2 |
| | 9 | 40 | 70 | 0.5 | 4.54 | 453.8 | 319.0 |
| K1 | | 161.96 | 478.26 | 496.66 | | | |
| K2 | | 344.40 | 541.83 | 478.63 | | | |
| K3 | | 989.40 | 475.67 | 520.47 | | | |
| R | | 827.50 | 66.16 | 41.84 | | | |

Note:
integrative score = solubility × 0.7 + drug content × 0.3.

complex of SBE-β-CD and DPT, DPT shows significant inhibition effects, wherein the inhibition effects on rat neurogliocytoma cell line (C6), human lung adenocarcinoma cell line (A-549), human leukemia cell line (HL-60), human erythremia cell line (K-562), human cervical cancer cell line (Hela) and human gastric cancer cell line (BGC-823) is significant better than that of Etoposide (its concentration is $10^{-5}$ to $10^{-8}$ M). There is no significant change observed relating to the inhibition effects on all of the strains as mentioned above of DPT within a concentration range of from $10^{-5}$ to $10^{-8}$ M, while the inhibition effects of Etoposide with the concentration range of from $10^{-5}$ to $10^{-8}$ M significantly decreased.

After the inclusion complex of SBE-β-CD and DPT is dissolved in physiological saline, the inhibition effects test by intravenous injection via tail vein on the transplanted tumor of mice S180 and Heps indicates that the tumor inhibition rates on S180 are 54.53% and 41.67% when the administration dosages of DPT are 10 and 5 mg/Kg respectively, and the tumor inhibition rates on Heps were 52.09% and 42.27% respectively, and significant inhibition effects can be observed; and the tumor inhibition effects are similar to those of the positive controls of cyclophosphamide (20 mg/Kg) and Etoposide (20 mg/Kg).

After the inclusion complex of SBE-β-CD and DPT is dissolved in water, the inhibition effects test on the growth of xenograft tumor for human non-small cell lung cancer by intravenous injection via tail vein into H460 nude mice shows that the tumor growth rate (T/C) is 49.68% and the tumor inhibiting rate is 43.08% when the administration dosage of DPT is 8 mg/Kg, and the drug exerts significant inhibition effects that are similar to those of the positive control of Etoposide (20 mg/Kg). The test indicates that the dosage groups of DPT have no significant inhibition effects on the body weight of the animals, while the body weight of the animals in the Etoposide group is significantly inhibited, indicating that the toxicity of DPT is lower than that of Etoposide.

The pharmacological tests for the inclusion complex of DPT and SBE-β-CD and the results are shown below.

The in vitro activity test for the DPT inclusion complex on different tumor cells:

The tumor strains are A-549 (human lung adenocarcinoma cell line), BGC-823 (human gastric cancer cell line), C-6 (rat neurogliocytoma cell line), Hep G2 (human hepatic cancer cell line), HL-60 (human leukemia cell line), K-562 (human erythremia cell line) and Hela (human cervical cancer cell line). The test article is the inclusion complex of DPT and SBE-β-CD (the content is 5.05%); the control is Etoposide injection (specification 5 ml:0.1 g, produced by Qilu Pharmaceutical Co., Ltd.). The drug was prepared as a stock solution of $10^{-2}$ M by using physiological saline and diluted into the test solution in a gradient composed of five concentrations: C1 $5\times10^{-5}$ M, C2 $10^{-5}$ M, C3 $10^{-6}$ M, C4 $10^{-7}$ M and C5 $10^{-8}$ M.

Experimental method: different tumor cells in exponential growth phase are inoculated in 96-well plates in a certain amount and the selected samples are added after the cells are cultured for 24 hours (suspension cells can be directly added after being inoculated), after the cells are incubated at 37° C. and 5% $CO_2$ for another 48 hours, MIT is added for further incubation for another 4 hours, and finally the samples are examined on a microplate reader after dissolving with DMSO. The results are shown in Table 7.

TABLE 7

Inhibition effects of DPT and Etoposide on the in vitro growth of seven kinds of tumor cells

| Name of the cell (name of the sample) | | Concentration of the sample | | | | |
|---|---|---|---|---|---|---|
| | | $5\times10^{-5}$M | $10^{-5}$M | $10^{-6}$M | $10^{-7}$M | $10^{-8}$M |
| A549 | DPT | 59.18% | 56% | 53.5% | 52.24% | 50.77% |
| | Etoposide | 68.67% | 22.99% | 5.18% | 3.68% | 2.3% |
| BGC-823 | DPT | 52.54% | 35.31% | 33.2% | 30.35% | 24.49% |
| | Etoposide | 61.14% | 10.55% | 8.15% | 7.67% | 3.41% |
| C6 | DPT | 84.41% | 58.54% | 55.01% | 54.11% | 52.34% |
| | Etoposide | 66.2% | 59.96% | 49.99% | 16.67% | 9.98% |
| HepG2 | DPT | 52.98% | 31.85% | 22.49% | 24.36% | 24.32% |
| | Etoposide | 97.14% | 38.94% | 8.71% | 2.02% | 1.71% |
| HL-60 | DPT | 57.37% | 39.41% | 36.83% | 29.27% | 14.96% |
| | Etoposide | 94.85% | 16.01% | 8.45% | 3.48% | 1.91% |
| hela | DPT | 62.68% | 49.89% | 47.9% | 46.57% | 42.9% |
| | Etoposide | 97.26% | 24.71% | 6.87% | 5.63% | 4.35% |
| K562 | DPT | 67.05% | 54.02% | 50.95% | 43.77% | 35.82% |
| | Etoposide | 67.32% | 15.04% | 4.45% | 3.08% | 2.38% |

The results show that DPT has significant inhibition effects on one kind of animal tumor cell and six kinds of human tumor cells, wherein the inhibition effects on rat neurogliocytoma cell line (C6), human lung adenocarcinoma cell line (A-549), human leukemia cell line (HL-60), human erythremia cell line (K-562), human cervical cancer cell line (Hela) and human gastric cancer cell line (BGC-823) are significant better than that of Etoposide (its concentration is from $10^{-5}$ to $10^{-8}$ M). The characteristics of its actions are as follows: there is no significant change on the inhibition effects of DPT on all of the strains as mentioned above within a range of $10^{-5}$ to $10^{-8}$ M, while the inhibition effects of Etoposide with the concentration range of $10^{-5}$ to $10^{-8}$ M significantly decreased.

The inhibition effects for the intravenous injection with DPT inclusion via ail vein on the transplanted tumor S180 and Heps of mice:

The test article: the inclusion complex of DPT and SBE-β-CD, the content of which is 5.05%, and it is prepared as the required concentration by using physiological saline.

Experimental groups: three dosage groups were set up for DPT, 10, 5 and 2.5 mg/kg; the blank control group: cyclophosphamide (CTX) group, Etoposide group 20 mg/kg.

Administration route: injection via tail vein, it is administered in a dosage of 0.4 ml/20 g body weight. Administration period: the drug is administrated 24 hours after the inoculation, once every two days for four times in total.

Experimental methods: 60 ICR mice with standard weight of from 18 to 22 g are inoculated with S-180 or Heps solid tumor according to the test method for transplanted tumors, hypodermic inoculation with 0.2 ml is carried out in the armpit in the anterior limb of every mouse. The body weight is determined 24 hours after the inoculation and they are randomly divided into six groups: the blank control group, the CTX group (20 mg/kg), the Etoposide group (20 mg/kg), the DPT group (10, 5 and 2.5 mg/Kg). The drug is administrated 24 hours after the inoculation once for every two days for 4 times, and tumor-bearing mice are killed on the next after drug withdrawal and their body weights are measured, and the separated tumor mess is weighed, and all of the data are subjected to statistical analyses (t-test). The results are shown in Table 8-9.

TABLE 8

The inhibition effects of DPT iv on the transplanted tumor Heps in mice ($\overline{X} \pm SD$) (n = 10)

| Groups | Dosage (mg/kg) | Body weight (g) Before administration | Body weight (g) After administration | Tumor weight (g) | Tumor inhibition rate (%) |
|---|---|---|---|---|---|
| NS |  | 21.30 ± 1.06 | 28.10 ± 4.58 | 1.97 ± 0.31 | 0.00 |
| CTX | 20 | 21.30 ± 1.49 | 22.50 ± 3.69** | 0.65 ± 0.21** | 66.94 |
| Etoposide | 20 | 21.10 ± 1.37 | 22.40 ± 2.41** | 0.80 ± 0.37** | 59.31 |
| DPT | 10 | 21.40 ± 0.84 | 22.90 ± 2.73** | 0.94 ± 0.32** | 52.09 |
| DPT | 5 | 20.80 ± 1.40 | 24.00 ± 3.46* | 1.14 ± 0.15** | 42.27 |
| DPT | 2.5 | 20.20 ± 1.48 | 24.50 ± 2.22* | 1.34 ± 0.29** | 32.10 |

*P < 0.05,
**P < 0.01 compared to the blank control group

The results show that the tumor inhibition rate of the DPT (10 and 5 mg/kg) groups for the transplanted tumor S180 in mice are 54.53% and 41.67% respectively compared to that in the blank control group, and these two dosages can significantly inhibit the growth of S180 tumor (P<0.01); with regard to the transplanted tumor Heps in mice, the tumor inhibition rate of the DPT (10 and 5 mg/kg) groups are 52.09% and 42.27% respectively compared to the blank control group, and these two dosages can significantly inhibit the growth of Heps tumor (P<0.01) and meet the requirements of the SFDA of China on the guidance for investigations on anti-tumor drugs (the inhibition rate should be higher than 40%). The antitumor effects are similar to that of the positive controls cyclophosphamide (20 mg/Kg) and Etoposide (20 mg/Kg).

TABLE 9

The inhibition effects of DPT iv on the transplanted tumor S180 of mice ($\overline{X} \pm SD$) (n = 10)

| Groups | Dosage (mg/kg) | Body weight (g) Before administration | Body weight (g) After administration | Tumor weight (g) | Tumor-inhibition rate (%) |
|---|---|---|---|---|---|
| NS |  | 19.50 ± 1.27 | 26.20 ± 2.10 | 1.84 ± 0.14 | 0.00 |
| CTX | 20 | 19.80 ± 1.69 | 23.00 ± 2.50** | 0.98 ± 0.22** | 46.77 |
| Etoposide | 20 | 19.30 ± 1.06 | 23.30 ± 1.83** | 1.05 ± 0.35** | 43.03 |
| DPT | 10 | 19.40 ± 1.71 | 22.50 ± 2.07** | 0.84 ± 0.27** | 54.53 |
| DPT | 5 | 19.00 ± 0.94 | 22.50 ± 2.55** | 1.08 ± 0.26** | 41.67 |
| DPT | 2.5 | 19.70 ± 1.16 | 24.90 ± 2.47 | 1.41 ± 0.30** | 23.44 |

*P < 0.05,
**P < 0.01 compared to the blank group

The inhibition effects of the DPT inclusion on the growth of xenograft tumor for human non-small cell lung cancer in nude mice:

The test article: the inclusion complex of DPT and SBE-β-CD, the content is 5.05%. Preparation Method: it is dissolved in a proper amount of saline after gentle shaking and the concentration is 0.4 mg/ml (which is the test solution for the 8 mg/kg group); other concentrations are prepared by diluting the stock solution of 0.4 mg/ml to the required concentration with physiological saline.

The control article: Etoposide injection produced by Qilu Pharmaceutical Co., Ltd. the batch number is 8060012EV, specification: 5 ml:0.1 g. Preparation Method: Etoposide injection is a kind of transparent sticky liquid and it is diluted with a proper amount of physiological saline and gently shaken and prepared as a homogeneous solution, and the concentration is 1 mg/ml.

Dosage setting: the high dosage group of DPT is 8 mg/kg, the medium dosage group of DPT is 4 mg/kg and the low dosage group of DPT is 2 mg/kg. The dosage for the positive control group of Etoposide injection is 20 mg/kg.

Experimental animals: source, germline and strain: BALB/c nude mice are provided by the Institute of Experimental Animals, Chinese Academy of Medical Sciences. Age: 35-40 days; body weight: 18-24 g; gender: male.

Transplanted tumor: the transplanted tumor for human nonsmall-cell lung cancer H460 in nude mice, and it is established by inoculating the human nonsmall-cell lung cancer H460 cell line hypodermically in the armpit of nude mice. $2 \times 10^6$ cells are inoculated.

Experimental Methods:

Human non-small cell lung cancer H460 cell line in exponential phase of growth is prepared as a cell suspension of $2 \times 10^7$/ml under sterile conditions, 0.1 ml thereof is inoculated hypodermically in the right armpit of nude mice. The diameters of the transplanted tumors in the nude mice are measured by a sliding caliper, and the animals are randomly divided into different groups when the tumors grow up to the amount of 100 to 300 mm³. The antitumor efficacy of the test article is dynamically observed by measuring the diameter of the tumor. The diameters of the tumor are determined once for every two days. The administration volume is 0.4 ml/20 g. The mice are killed 21 days after administration, and the tumors are surgically isolated and weighed. The calculation formula for tumor volume (TV) is as follows:

$$TV = \frac{1}{2} \times a \times b^2$$

Wherein a and b represents for the length and the width, respectively.

The relative tumor volume (RTV) is calculated according to the measured results, and the calculation formula is as follows: RTV=Vt/V0. Wherein V0 is the tumor size measured during grouping and drug administration (d0), Vt is the tumor size in every measurements. The evaluation parameter for antitumor activity is the relative tumor growth rate T/C (%) which is calculated according to the formula as follows:

$$T/C(\%) = \frac{TRTV}{CRTV} \times 100$$

TRTV: the treatment group RTV; CRTV: the negative control group: RTV.

Results:

The results of experimental therapy on the transplanted tumor of human non-small cell lung cancer H460 in nude mice by DPT are shown in Table 10 and 11. DPT is administered in a dosage of 8 mg/kg by intravenous injection via tail vein three times a week, 9 times in total, and the T/C (%) for the transplanted tumor of human non-small cell lung cancer H460 in nude mice is 49.68%; the tumor inhibition rate is 43.08%. Different dosages of DPT in the groups have no significant inhibition effects on the body weight of the animals.

The positive control Etoposide injection was intravenously injected via tail vein in a dosage of 20 mg/kg three times a week for 9 times in total, the T/C (%) for the transplanted tumor of human non-small cell lung cancer H460 in nude mice is 32.18%; the tumor inhibition rate is 61.08%. However, it has significant inhibition effects on the body weight of the animals and exerts an obvious toxicity.

Conclusions:

The results for the T/C and the tumor-inhibition rate of DPT on the transplanted tumor of human non-small cell lung cancer H460 in nude mice show that DPT has significant inhibition effects on the growth of the transplanted tumor of human nonsmall-cell lung cancer H460 in nude mice and DPT has a good anticancer activity which meets the requirements of SFDA of China on the efficacy of new anti-tumor drugs (T/C<60%, tumor inhibition rate>40%), and its toxicity is relatively mild.

TABLE 10

The inhibition effects of DPT on the growth of the xenograft tumor of human nonsmall-cell lung cancer H460 in nude mice (X ± SD)

| Groups | Dosage (mg/kg) | Initial body weight (g) | Initial number of animals | Ending body weight (g) | Ending number of animals | Tumor weight (g) | Tumor-inhibition rate (%) |
|---|---|---|---|---|---|---|---|
| Blank control group | — | 22.83 ± 1.60 | 6 | 25.61 ± 2.32 | 6 | 3.25 ± 0.91 | — |
| Etoposide group | 20 | 22.67 ± 1.37 | 6 | 16.82 ± 2.06** | 6 | 1.27 ± 0.61** | 61.08 |
| High dosage group of DPT | 8 | 22.33 ± 1.51 | 6 | 22.55 ± 2.50 | 6 | 1.85 ± 0.95* | 43.08 |
| Medium dosage group of DPT | 4 | 23.33 ± 2.25 | 6 | 23.32 ± 2.08 | 6 | 2.52 ± 0.92 | 22.56 |
| Low dosage group of DPT | 2 | 22.50 ± 1.38 | 6 | 25.32 ± 2.25 | 6 | 2.94 ± 0.68 | 9.49 |

Compared to the blank control group, *P < 0.05, **P < 0.01

TABLE 11

Effects of DPT on the changes in growth volume of xenograft tumors of human nonsmall-cell lung cancer H460 in nude mice (X ± SD, n = 6, tumor volume: unit: mm$^3$)

| Groups | Dosage mg/kg | 0 d Tumor volume | 2 d Tumor volume | 2 d RTV | 2 d T/C (%) | 4 d Tumor volume | 4 d RTV | 4 d T/C (%) |
|---|---|---|---|---|---|---|---|---|
| Blank control group | — | 275 ± 117 | 417 ± 125 | 1.608 ± 0.390 | — | 678 ± 234 | 2.611 ± 0.809 | — |
| Etoposide group | 20 | 275 ± 130 | 352 ± 169 | 1.306 ± 0.356 | 81.24 | 534 ± 277 | 2.012 ± 0.744 | 77.07 |
| High dosage group of DPT | 8 | 247 ± 108 | 313 ± 151 | 1.248 ± 0.113 | 77.61 | 430 ± 196 | 1.721 ± 0.287 | 65.92 |
| Medium dosage group of DPT | 4 | 272 ± 131 | 381 ± 234 | 1.324 ± 0.236 | 82.37 | 521 ± 288 | 1.823 ± 0.427 | 69.82 |
| Low dosage group of DPT | 2 | 296 ± 117 | 427 ± 190 | 1.396 ± 0.251 | 86.85 | 554 ± 234 | 1.827 ± 0.373 | 69.97 |

TABLE 11-continued

Effects of DPT on the changes in growth volume of xenograft tumors of human nonsmall-cell lung cancer H460 in nude mice (X ± SD, n = 6, tumor volume: unit: mm³)

|  |  | 6 d | | | 8 d | | |
|---|---|---|---|---|---|---|---|
|  |  | Tumor volume | RTV | T/C (%) | Tumor volume | RTV | T/C (%) |
| Blank control group | — | 787 ± 247 | 3.063 ± 0.831 | — | 1197 ± 557 | 4.391 ± 0.819 | — |
| Etoposide group | 20 | 531 ± 186 | 2.048 ± 0.441 | 66.86 | 539 ± 255 | 2.054 ± 0.776 | 46.77 |
| High dosage group of DPT | 8 | 559 ± 179 | 2.403 ± 0.652 | 78.45 | 635 ± 183 | 2.747 ± 0.766 | 62.55 |
| Medium dosage group of DPT | 4 | 729 ± 471 | 2.465 ± 0.699 | 80.49 | 906 ± 434 | 3.331 ± 0.641 | 75.85 |
| Low dosage group of DPT | 2 | 729 ± 364 | 2.391 ± 0.764 | 78.07 | 807 ± 294 | 2.819 ± 0.559 | 64.20 |

|  |  | 10 d | | | 12 d | | |
|---|---|---|---|---|---|---|---|
|  |  | Gross tumor volume | RTV | T/C (%) | Gross tumor volume | RTV | T/C (%) |
| Blank control group | — | 1315 ± 619 | 5.002 ± 1.550 | — | 1923 ± 816 | 7.428 ± 2.593 | — |
| Etoposide group | 20 | 482 ± 216 | 1.846 ± 0.688 | 36.90 | 534 ± 254 | 2.189 ± 1.212 | 29.47 |
| High dosage group of DPT | 8 | 895 ± 252 | 3.853 ± 0.732 | 77.03 | 1034 ± 246 | 4.548 ± 1.106 | 61.23 |
| Medium dosage group of DPT | 4 | 1052 ± 475 | 4.041 ± 1.493 | 80.78 | 1261 ± 586 | 4.780 ± 1.070 | 64.35 |
| Low dosage group of DPT | 2 | 1039 ± 316 | 3.750 ± 1.015 | 74.96 | 1424 ± 511 | 5.122 ± 1.538 | 68.96 |

|  |  | 14 d | | | 16 d | | |
|---|---|---|---|---|---|---|---|
|  |  | Tumor volume | RTV | T/C (%) | Tumor volume | RTV | T/C (%) |
| Blank control group | — | 2242 ± 1045 | 8.486 ± 2.330 | — | 2675 ± 1360 | 9.974 ± 2.844 | — |
| Etoposide group | 20 | 682 ± 311 | 2.898 ± 1.741 | 34.16 | 730 ± 384 | 3.115 ± 1.969 | 31.23 |
| High dosage group of DPT | 8 | 1122 ± 368 | 4.845 ± 1.330 | 57.10 | 1132 ± 397 | 4.955 ± 1.786 | 49.68 |
| Medium dosage group of DPT | 4 | 1530 ± 572 | 5.954 ± 1.425 | 70.16 | 1740 ± 637 | 6.870 ± 1.613 | 68.88 |
| Low dosage group of DPT | 2 | 1777 ± 386 | 6.698 ± 2.532 | 78.93 | 2249 ± 394 | 8.626 ± 3.791 | 86.49 |

|  |  | 18 d | | | 21 d | | |
|---|---|---|---|---|---|---|---|
|  |  | Tumor volume | RTV | T/C (%) | Tumor volume | RTV | T/C (%) |
| Blank control group | — | 3058 ± 1655 | 11.270 ± 3.067 | — | 3082 ± 1541 | 11.517 ± 3.202 | — |

TABLE 11-continued

Effects of DPT on the changes in growth volume of xenograft tumors of human nonsmall-cell lung cancer H460 in nude mice (X ± SD, n = 6, tumor volume: unit: mm³)

| | | | | | | | |
|---|---|---|---|---|---|---|---|
| Etoposide group | 20 | 873 ± 407 | 3.876 ± 2.645 | 34.39 | 872 ± 305 | 3.706 ± 1.796 | 32.18 |
| High dosage group of DPT | 8 | 1292 ± 340 | 5.609 ± 1.197 | 49.77 | 1375 ± 558 | 5.721 ± 0.925 | 49.68 |
| Medium dosage group of DPT | 4 | 1891 ± 664 | 7.697 ± 2.279 | 68.30 | 1945 ± 586 | 7.832 ± 1.816 | 68.01 |
| Low dosage group of DPT | 2 | 2304 ± 405 | 8.825 ± 3.701 | 78.31 | 2591 ± 412 | 9.776 ± 3.452 | 84.89 |

EMBODIMENTS

Embodiment 1

100 mL of 30% HP-β-CD aqueous solution is transferred into a 500 ml of Wolff glass bottle and heated on a water bath to keep its temperature at 50±5° C., 44 ml of 10% DPT ethanol solution is dropped while agitating, and the solution is incubated and then agitated for another 1 hour, and the evaporated ethanol is collected at the same time. It is filtrated with 0.45 μm filter membrane in hot state, the filtrate is subjected to membrane spinning decompressed concentration, the viscous substance is subjected to vacuum to for dehydration and 33.6 g white mesh is obtained. The content of DPT is determined by ultraviolet spectrophotometry and the result is 12.12%; the solubility of DPI in the inclusion complex in water is 84.1% (mg/ml) by the method in the examples of Chinese Pharmacopoeia 2005.

Embodiment 2

Preparation of Compound 2

100 mL of 30% SBE-β-CD aqueous solution is transferred into a 200 ml of Wolff glass bottle and heated on a water bath to keep its temperature at 50±5° C., 37.3 ml 10 DPT acetone solution is dropped while agitating, and the solution is incubated and then agitated for another 2 hours, then it is kept still at room temperature for 2 hours and filtrated with 0.45 μm filter membrane in hot state. The filtrate is pre-frozen for 12 h and lyophilized at −45° C. for 48 h. 62.9 g white porous solid is obtained. The content of DPT is determined by ultraviolet spectrophotometry and the result is 5.05%; the solubility of DPT in the inclusion complex in water is 460% (mg/ml) by the method in the examples of Chinese Pharmacopeia 2005.

Figure 1:
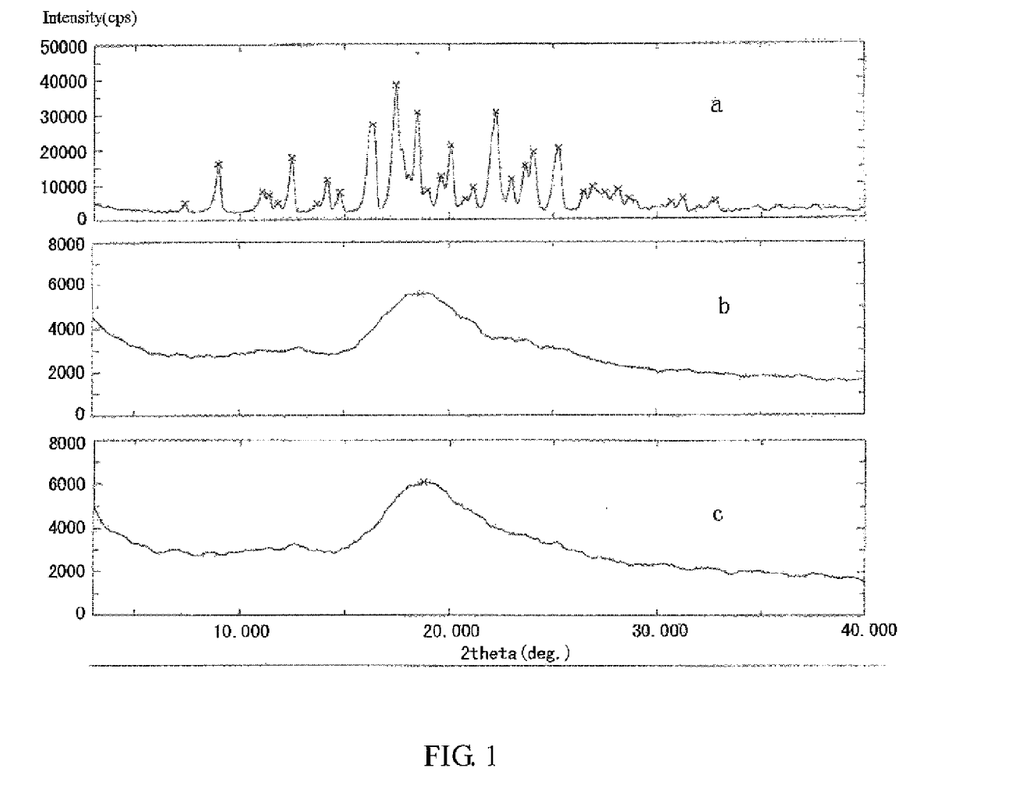
FIG. 1 is the X-ray powder diffraction spectrum for DPT (a), SBE-β-CD (b) and its inclusion complex (c)
Figure 2:
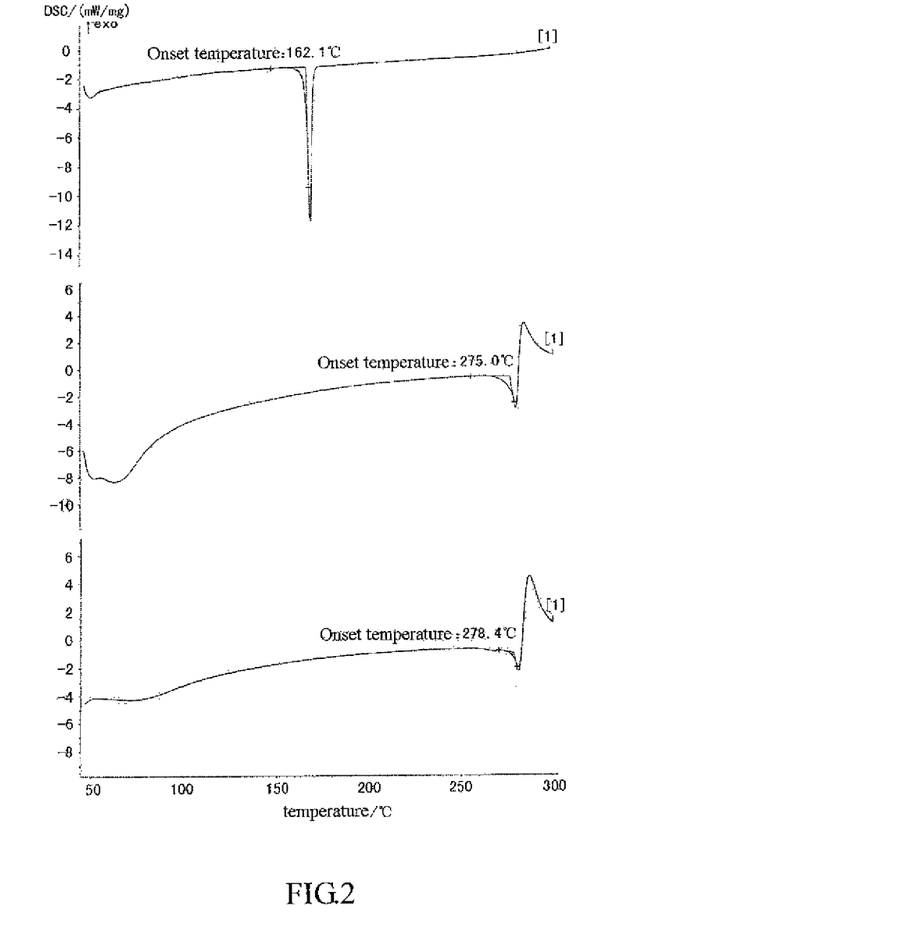
FIG. 2 is the figure for differential scanning calorimetry of DPT (a), SBE-β-CD (b) and its inclusion complex (c).

The X-ray powder diffraction spectrum for the inclusion complex of DPT-SBE-β-CD is shown in FIG. 1 and the figure for differential scanning calorimetry (DSC) is shown in FIG. 2. The results show that the compound has been obtained.

The invention claimed is:

1. An inclusion complex of deoxypodophyllotoxin and β-cyclodextrin derivative, wherein the molar ratio of deoxypodophyllotoxin to β-cyclodextrin derivative is from 1:1.00 to 1:8.06, wherein the β-cyclodextrin derivative is sulfobutyl ether-β-cyclodextrin or hydroxypropyl β-cyclodextrin.

2. The inclusion complex as claimed in claim 1, wherein the β-cyclodextrin derivative is sulfobutyl ether-β-cyclodextrin.

3. The inclusion complex as claimed in claim 2, wherein the molar ratio of deoxypodophyllotoxin to sulfobutyl ether-β-cyclodextrin is from 1:2.33 to 1:6.42.

4. The inclusion complex as claimed in claim 1, wherein the β-cyclodextrin derivative is hydroxypropyl β-cyclodextrin.

5. The inclusion complex as claimed in claim 4, wherein the molar ratio of deoxypodophyllotoxin to hydroxypropyl β-cyclodextrin is from 1:2.24 to 1:6.35.

6. A method for inhibiting tumor cell growth which comprises administering the inclusion complex as claimed in claim 1 to treat small cell lung cancer, malignant lymphoma, malignant germinal tumor, leukemia, neurogliocytoma, cervical cancer, non-small cell lung cancer, gastric cancer or hepatic cancer.

* * * * *